US009205280B2

(12) United States Patent
Bertram et al.

(10) Patent No.: US 9,205,280 B2
(45) Date of Patent: Dec. 8, 2015

(54) METHOD AND APPARATUS FOR PLANNING OR CONTROLLING A RADIATION TREATMENT

(75) Inventors: Pascal Bertram, Munich (DE); Claus Promberger, Pfaffenhofen (DE); Thomas Flurschuetz, Munich (DE)

(73) Assignee: Brainlab AG, Feldkirchen (DE)

( * ) Notice: Subject to any disclaimer, the term of this patent is extended or adjusted under 35 U.S.C. 154(b) by 185 days.

(21) Appl. No.: 14/000,265

(22) PCT Filed: May 25, 2011

(86) PCT No.: PCT/EP2011/058523
§ 371 (c)(1),
(2), (4) Date: Aug. 19, 2013

(87) PCT Pub. No.: WO2012/159671
PCT Pub. Date: Nov. 29, 2012

(65) Prior Publication Data
US 2013/0324785 A1    Dec. 5, 2013

(51) Int. Cl.
*A61N 5/10* (2006.01)
*G06F 19/00* (2011.01)
*G06T 15/06* (2011.01)
*G06T 15/08* (2011.01)

(52) U.S. Cl.
CPC .............. *A61N 5/1039* (2013.01); *A61N 5/103* (2013.01); *A61N 5/1048* (2013.01); *G06F 19/3481* (2013.01); *G06T 15/06* (2013.01); *G06T 15/08* (2013.01); *A61N 2005/1061* (2013.01)

(58) Field of Classification Search
CPC ........... A61N 2005/1061; A61N 5/103; A61N 5/1039; A61N 5/1048; A61N 5/1042; A61N 5/1031; A61N 5/1047; A61N 5/1049; A61N 2005/1087; A61N 5/10; A61N 5/1037; A61N 5/1067; A61N 2005/1052; A61N 2005/1062; A61N 5/1081; A61N 2005/1055; G06F 19/3481; G06T 15/06; G06T 15/08
USPC ................................................ 378/65, 62, 98
See application file for complete search history.

(56) References Cited

U.S. PATENT DOCUMENTS

| 7,295,649 | B2 * | 11/2007 | Johnsen | 378/65 |
| 8,044,359 | B2 * | 10/2011 | Simon | 250/370.07 |
| 2003/0068009 | A1 * | 4/2003 | Xing | 378/65 |
| 2005/0116172 | A1 * | 6/2005 | Trinkaus et al. | 250/363.02 |

FOREIGN PATENT DOCUMENTS

| EP | 0 673 661 | 9/1995 |
| WO | 2004/067091 | 8/2004 |
| WO | 2009/137794 | 11/2009 |

OTHER PUBLICATIONS

International Search Report for International Application No. PCT/EP2011/058523 dated Jan. 12, 2012.

* cited by examiner

*Primary Examiner* — Irakli Kiknadze
(74) *Attorney, Agent, or Firm* — Tucker Ellis LLP

(57) ABSTRACT

The present invention relates to method for generating planning data or control data for a radiation treatment, comprising the following steps: acquiring segmented data of an object which contains a treatment volume and a non-treatment volume; modelling at least some or all of the volume or surface of the treatment volume as a source of light or rays exhibiting a predefined or constant initial intensity; modelling the non-treatment volume as comprising volumetric elements or voxels which each exhibit an individually assigned feature or attenuation or transparency value ($t_{min} \leq t \leq t_{max}$) for the light or rays which feature is assigned to the light or ray or which attenuation or transparency maintains or reduces the intensity of the light or ray as it passes through the respective volumetric element or voxel, wherein the feature or attenuation or transparency value is individually assigned to each volumetric element or voxel of the non-treatment volume; defining a map surface which surrounds the treatment volume or the object; calculating an accumulated intensity value for points or areas on the map surface, the accumulated intensity being the sum of the intensities of all the rays which exhibit the predefined or constant initial intensity and are emitted from the volume or surface of the treatment volume and reach a respective point on the map surface preferably by following a straight line, wherein if the ray passes through a non-treatment volume or voxel, the intensity of the respective ray is reduced or attenuated by a factor which is determined by the individual feature or attenuation or transparency value of the respective non-treatment volume or voxel; and generating an intensity distribution on the map surface using the calculated accumulated intensities.

19 Claims, 4 Drawing Sheets

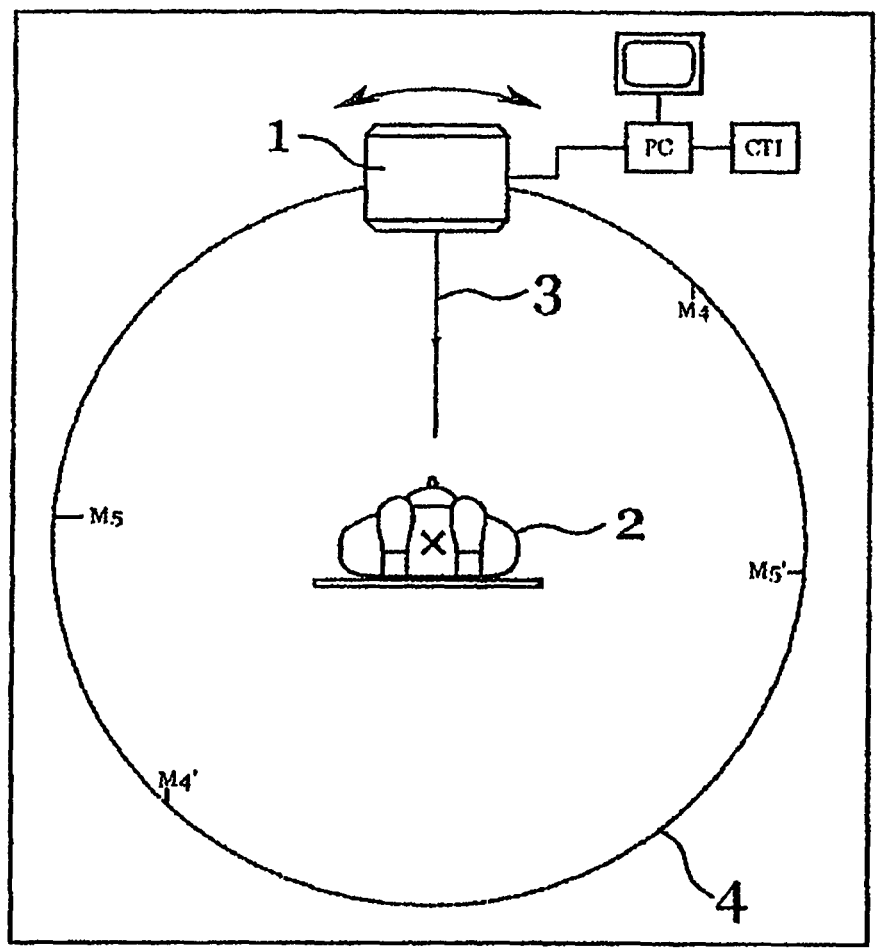

METHOD AND APPARATUS FOR PLANNING OR CONTROLLING A RADIATION TREATMENT

This application is a national phase of International Application No. PCT/EP2011/058523 filed May 25, 2011 and published in the English language.

The present invention relates to a method and an apparatus for planning or controlling a radiation treatment, such as for example a tumour radiation treatment, wherein the tumour may be surrounded by or located next to healthy tissue or organs which are to be protected and/or only minimally affected by the radiation treatment.

In particular, this invention relates to radiation therapy planning and radiation therapy equipment for the treatment of tumours or the like and specifically to a radiation therapy planning method for calculating or determining good or optimum points or areas on an object or a patient to be treated for delivering radiation in order to achieve the desired treatment at a treatment area within the object or patient while avoiding damage to tissue or organs to be protected or at least reducing or minimising the impact of said radiation on areas or volumes to be protected.

Radiation therapy refers to the treatment of a specific tissue, for example a tumourous tissue, using externally or internally applied high-energy radiation. The direction and placement of the radiation must be accurately controlled in order to ensure both that the treatment volume or tumour receives a desired or sufficient amount of radiation in order to be treated or destroyed and that damage or negative effects to the surrounding healthy or non-tumourous tissue is/are avoided or minimised.

An external-source radiation therapy, as preferably used in the present invention, uses a radiation source which is external to the patient—typically either a radioisotope or a high-energy x-ray source such as a linear accelerator. The external source produces a collimated beam which is directed onto and into the patient in order to reach the treatment volume or tumour site. In most cases, however, an external-source radiation therapy also undesirably but necessarily irradiates a volume of non-tumourous or healthy tissue lying in the path of the radiation beam along with the tumourous tissue or treatment volume.

The adverse effect of irradiating healthy tissue can be reduced, while still maintaining a given dose of radiation in the tumourous tissue or treatment volume, by projecting the external radiation beam into the patient at a variety of gantry angles with the beams converging on the tumour site. It is then desirable to obtain information concerning one or more preferred directions and/or entry points of the radiation beam with respect to a patient or body, so that a significant amount of the energy delivered by the radiation beam from these directions and/or at these entry points is delivered to the treatment volume or tumourous tissue, while healthy tissue or organs located next to the treatment volume and/or at least partly surrounding the treatment volume are not or only minimally affected by the radiation beam.

U.S. Pat. No. 5,418,827 discloses a method for radiation therapy planning, wherein a distribution of electrical charges within a conductor is determined which would produce a potential energy field which matches the desired dose to the tumour in the plane of the radiation therapy machine. The fluence of any given ray through the tumour is determined by summing the charges along the ray's path.

It is an object of the present invention to provide a method and an apparatus for improving the planning or controlling of a radiation therapy treatment.

This object is solved by the subject-matter of the independent claims. Advantageous aspects of the invention are disclosed in the following and contained in the subject-matter of the dependent claims. Different advantageous features can be combined in accordance with the invention wherever this is technically expedient and feasible.

In accordance with a method for generating data or information for planning a radiation treatment or for controlling a radiation treatment, for example by controlling the operation of a radiation device which is known in its own right, data of the body or object to be treated are acquired. The data are preferably 3D data or volumetric data which can be obtained by known imaging methods which generate image data of anatomical structures, such as the soft tissue, bones, organs, etc. of a body. A medical imaging method can be an apparatus-based imaging method, such as for instance computed tomography (CT), cone beam computed tomography (CBCT, in particular volumetric CBCT), x-ray tomography, magnetic resonance tomography (MRT or MRI), sonography, ultrasound examination, positron emission tomography or any other imaging method which generates a three-dimensional data set as an output which is a representation of the imaged object or body.

The data used by the method according to the invention are either already segmented or are to be segmented for example using known methods such as atlas segmentation. An atlas typically consists of a plurality of generic models of objects, wherein the generic models of the objects together form a complex structure. When segmenting medical images, the atlas is matched to medical image data and the image data are compared with the matched atlas in order to assign a point (such as a pixel or voxel) of the image data to an object of the matched atlas, thereby segmenting the image data into objects such as for example bones, organs, blood vessels, nerves and so on.

Some anatomical structures are unlikely to be fully and/or easily detectable using atlas segmentation. In particular, pathological changes in tissue structures, such as tumours, may not be easily detectable and may not be visible in images generated by the imaging methods mentioned. However, these structures—such as primary/high-grade brain tumours—can be made visible in MRI scans by using contrast agents to infiltrate the tumour. In the case of MRI scans of brain tumours, the signal enhancement in the MRI images due to contrast agents infiltrating the tumour can be considered to represent the solid tumour. Thus, a tumour can be detected and can in particular be discerned in the image generated by the imaging method.

Any way of providing segmented data can be used, including for example a combination of atlas segmentation and images taken while using contrast agents.

The area or volume to be treated, such as for example tumourous tissue or a tumour, is referred to in the following as a "treatment volume" and is formed as a treatment volume model within the above-mentioned image data. If a tumour is located in or adjacent to surrounding tissue, the whole tumour or tumourous tissue is modelled as a treatment volume comprising a treatment volume surface which separates the treatment volume from the surrounding and/or adjacent tissue or structures of the object or body, which then represent a non-treatment volume.

In accordance with the invention, the treatment volume and advantageously (e.g. to reduce the computing time) only the surface of the treatment volume is considered or modelled as a preferably continuous source of rays, such as light, or as an illuminant which emits light or rays, all rays preferably having the same initial intensity value of for example 100, along one or more straight lines or paths in the direction of the outside of the body within which the treatment volume is located, i.e. simulated rays are projected from the treatment volume or tumour to the outside. The treatment volume or tumour can be considered as a volumetric light source. Alternatively, the treatment volume or the treatment volume surface is modelled or considered to have a number of areas or point-shaped sources of light or rays or ray starting points which are distributed uniformly or randomly across the treatment volume surface or even within the treatment volume. The light or rays start or emerge from the treatment volume surface and spread out in every direction, preferably with the exception of the treatment volume itself, i.e. light or rays emitted from the treatment volume surface preferably do not pass through the treatment volume itself.

If some parts or areas of the treatment volume shall receive a higher dose of irradiation during later radiation treatment, such as e.g. malignant parts of a tumour, the initial intensity value of the rays emerging from the tumour or its surface can be increased (to be e.g. 150) compared to rays emerging from non-malignant parts of the tumour. The rate of cell division of a tumour can be used to determine the initial intensity value, so the initial intensity value can for example be a (linear) function of the rate of cell division.

It is to be noted that the terms "light", "ray", "opacity", "transparency" and "intensity" as used here do not refer to actual optical arrangements or processes but rather to simulation or calculation methods.

The non-treatment volume which is adjacent to and/or surrounds at least a part of the treatment volume is segmented as mentioned before, and the segmented elements such as organs, blood vessels, nerves and so on are considered or modelled in accordance with the invention, in order to have an assigned feature, such as to reduce the intensity of a transient ray by a predetermined absolute factor or by a factor per unit length. The non-treatment volume can be considered to have an at least partially transparent volume or area which exhibits an individual transparency or transparency distribution which can also be considered to have the opposite property, i.e. an opacity distribution. So-called organs at risk (OARs) are for example modelled to have a relatively low transparency, in order to largely reduce the intensity of a transient ray, or even to be opaque so as not to allow light or a ray to pass through (i.e. the intensity of the exiting ray is 0). Organs or (tissue) structures which are less affected by radiation are for example modelled or considered to have a relatively high transparency (for example 0.8 to 1), i.e. for example these organs or structures allow light or rays emitted from the treatment volume surface to pass through with no attenuation or intensity reduction (i.e. transparency=1) or with only relatively little attenuation or intensity reduction. In order to model structures or organs as having a respective individual and probably uniform (within the structure) and predefined feature, such as a transparency, a volume element (voxel) belonging to the respective structure or organ can be defined as having a specifically assigned predefined feature, such as a transparency or opacity. A specific organ or structure is for example formed or modelled by voxels which all have the same transparency or opacity within the volume of the structure or organ.

By using a continuous or almost continuous representation of the organ coverage information, the tumour extent is rendered in the image. Using volumetric rendering, the distance from the tumour and the outer contour can also be included. This continuous map allows algorithms to easily find local and global minima for organ coverage.

Once the structures or organs of interest or the entire non-treatment volume which is adjacent to and/or surrounds at least a part of the treatment volume is modelled to have a respective individual feature, such as a transparency or transparency distribution, which can for example be accomplished by defining the transparency or opacity of the relevant voxels (for example only organs at risk) or of each voxel of the volume of the body except the treatment volume, the light or light intensity or rays which reach the outside of a body to be treated are calculated, or an area such as a sphere is calculated which surrounds the treatment volume and preferably has its centre at the intended isocentre located within the treatment volume. The isocentre can be the centre of mass of the treatment volume. This area or sphere is referred to as a "map surface" or "collision map".

In order to calculate the projection or intensity of the light or rays which are emitted from the treatment volume itself, for example the barycentre, or the treatment volume surface, and reach the outside surface of the body or an area, such as a sphere, surrounding the treatment volume or the body, the paths of several rays have to be considered. A calculation or simulation is performed in order to ascertain which of the above-mentioned modelled non-treatment structures exhibiting an individually assigned feature, such as a transparency/opacity, or voxels with an individually assigned feature, such as a transparency/opacity, are passed along a straight line of the ray, wherein these structures or voxels all influence the light rays or attenuate the intensity of the light or rays emitted from the treatment volume surface, for example by a factor of between 0 and 1. Alternatively, the respective features(s) are assigned to the light or rays passing the non-treatment structures or voxels having these individually assigned feature(s). Using this approach, light or rays emitted from the tumour are shadowed by the surrounding OARs. This simplified problem is similar to a problem experienced in computer graphics, namely that of calculating the shadows of volumetric light. Each ray or light beam is ever increasingly attenuated as it passes through areas exhibiting a transparency other than 1, i.e. each ray or light beam is affected by all the transparency or opacity values on its way to reaching the outer surface. If, for example, a ray is emitted from the treatment volume surface which has a predefined simulated initial intensity of 100, and this ray passes along a first distance $d_1$ which includes an organ at risk (see OAR1 in FIG. 1) exhibiting an assigned predefined transparency (of $t_1$/unit length), then this ray is attenuated by: $d_1 \cdot t_1$/unit length. The (virtual) intensity of this ray as it exits the respective structure is then given by:

$$I_{exit} = I_{center} d_1 \cdot t_1 / \text{unit length}$$

This calculation can be repeated if more structures or organs exhibiting a predefined transparency of for example t<1 are also situated in the path of the respective ray. The transparency t of a structure or voxel which is not or not appreciably affected by radiation can be set to 1.

Although possible, it is preferred if physical effects such as deflection, reflection, diffusion or scattering of the rays or light beams are not considered. A calculation is preferably performed in order to ascertain how rays or light beams which are emitted from the treatment volume surface and exhibit for example an initial intensity of 100 are attenuated by the respective transparent (t=1) or semitransparent (0<t<1) or opaque (t=0) volumes or voxels which exhibit an individually assigned transparency or opacity (o=1-t) while following a straight line on their way from the outer surface of the treatment volume to the surface onto which said rays are incident, such as a sphere centred around the treatment volume or a barycentre of the treatment volume, all or at least some of the surface of which is preferably outside the body within which the treatment volume is located. The outer surface or sphere which is considered as a map surface will then have an intensity distribution formed by the (probably attenuated) intensities of all the rays which reach this outer surface or sphere. It is to be noted that more than one ray can reach a single point of the outer surface or sphere, since the rays preferably do not start at a single point but rather from some or all of the points of the treatment volume, preferably in a distribution across the outer surface of the treatment volume.

When modelling the treatment volume or its surface as a source of light, this volume or surface can be modelled either as a homogenously illuminated or illuminating volume or surface or as a plurality of light-emitting points which are preferably evenly distributed over the volume or surface or distributed over the volume or surface using Monte Carlo techniques.

Once all the rays or light beams emitted from the entire volume or surface of the treatment volume or from all the emitting points distributed within the volume or over the treatment volume surface have been considered, and all the effects of at least partially transparent or opaque volumes or voxels along the straight path of the light or beams from the treatment volume surface to the map surface have been calculated, an intensity image or labelled image based on all these rays is calculated, wherein each point on the map surface is assigned an intensity or colour value depending on the amount of the intensities of all the rays or light beams reaching this point. If, for example, an organ to be protected from irradiation is on the path of all the beams emitted from the treatment volume surface to a specific part of the map surface, then this part of the map surface will for example receive no ray exhibiting an intensity greater than 0 and will thus for example appear black, whereas a map area will for example appear white if there is no organ at risk between the treatment volume surface and the corresponding map surface, i.e. a number of rays with an unattenuated intensity of for example 100 reach this point and are then summed to for example 100 (number of rays reaching said point). Depending on the summed or integrated amount of transparent volumes or opaque voxels in the path of all the light beams reaching the map surface, the intensities or colour values of the map surface points or pixels can have any intermediate value between a minimum, for example 0% (indicating for example an improper point for irradiation), and a maximum value, for example 100% (indicating for example an optimum point for irradiation), in order to indicate what amount of non-transparent or semi-transparent volumes (i.e. organs to be protected) are situated on the path from the treatment volume surface to the respective map surface area or point.

The accumulated intensity of a map surface point can for example be defined as $$I_{map} = \Sigma I_i;$$

wherein $\Sigma I_i$ is the sum of the intensities of all the rays reaching this map surface point.

If the respective non-treatment structures or volumes do not have a fixed assigned value or feature, such as a predefined opacity, the accumulated intensity $I_{map}$ can be calculated to be a function of variables, such as variable opacities, so that e.g. the individual OARs can be given different weights or opacities after calculating the (variable) intensities of the map surface.

The highest value of the accumulated intensity of all the map surface points can be defined as 100% (or as being "light", see for example FIGS. 1 and 3).

It is to be noted that a single point on the map surface can be reached not only by a single ray emitted from a single point on the treatment volume surface but also by additional rays and, depending on the internal opacity or transparency of the body volume structure, possibly even by all the rays emitted from the treatment volume.

Alternatively, all rays emitted from the treatment volume surface on the side of the treatment volume surface on which the point of the map surface is located are considered. For example, in this case only the rays emitted from the rear side of the treatment volume surface with respect to a point on the map surface will not reach this map surface point, since the treatment volume itself can in such an alternative embodiment be considered to be fully opaque, i.e. does not allow any ray emitted from the treatment volume surface to pass through the treatment volume itself.

The colour or shadow or intensity image thus generated on the map surface can be interpreted as indicating the extent to which tissue is to be protected, which is then consequently modelled as exhibiting a specific transparency or opacity (i.e. for example opaque if it is to be fully protected, 20% to 80% transparency if it is expediently protected, and fully transparent if it need not be protected) which is then effected when irradiating the treatment volume with a ray projected from the respective map surface point onto the treatment volume or its centre (i.e. the reverse direction of the above-mentioned simulation).

However, this scenario only covers the unrealistic prospect that the radiation stops within the treatment volume.

Since a treatment ray will have a certain (desired) effect within the treatment volume, but will still emerge from the treatment volume, it is necessary to consider not only the intensity value of a pixel or area on the map surface but also the intensity value on the opposite side, for example the point on the map or sphere surface which is the exit point of the irradiation ray when radiation is delivered through the entry point on the map surface and passes through the treatment volume. If the map surface is modelled as a sphere, the exit point is the point obtained when mirroring the entry point at the centre point of the sphere, which is preferably the centre of mass of the treatment volume.

In order to determine whether or not it is expedient to irradiate the treatment volume with a ray emanating from or passing through a point on the map surface, the accumulated intensities of all the incoming rays at both the entry point and the (mirrored) exit point are preferably considered. In its simplest form, the two accumulated intensities can be added, such that one hemisphere of the map surface shows a distribution of accumulated intensities and the other hemisphere shows the intensity distribution mirrored at the centre of the sphere.

If there is any tissue or organ or volume in the line of the radiation beam which is to be protected or less affected, this volume to be protected is preferably located behind the treatment volume (i.e. the radiation beam passes through the front non-treatment volume first, then passes—probably with a low attenuated irradiation intensity—through the treatment volume, and then—with an even further reduced irradiation intensity—through the tissue or organ or volume to be protected), hence it is advantageous to not simply sum the accumulated intensities of the simulated rays which reach an entry point and the corresponding exit point of a radiation beam, but rather to also take into account whether or not volume to be protected is located in front of or behind the treatment volume. For this purpose, the intensities at corresponding (mirrored) entry and exit points should only be the same if the same amount of opaque volume or voxels is located between one (entry or exit) point and the treatment volume as is located between the other (exit or entry) point and the treatment volume. In all other cases, it is advantageous for the accumulated intensity of a map surface point to be higher at the point which has less opaque volume (to be protected) between this point and the treatment volume, as compared to the amount of opaque volume located between the treatment volume and the opposing (mirrored) point which is then designated as the exit point. In order to achieve this result, the accumulated intensity at one point is compared to the accumulated intensity at the opposite (mirrored) point, and if the first intensity is higher than the accumulated intensity at the mirrored point, this indicates that irradiation should preferably be started from this point and not from the opposite point, since more of the volume or tissue to be protected will then be located behind and not in front of the treatment volume. This can be indicated or made visible by for example adding a predefined amount of (simulated light) intensity to the added or integrated amount of intensity at the point on the map surface exhibiting a higher total value for the accumulated intensity or by subtracting a predefined amount of (light) intensity from the opposite map surface point, for example:

If $I_{map,1}$ is the accumulated intensity at a map surface point and $I_{map,2}$ is the accumulated intensity at the opposite or mirrored point, the following calculation for the resulting map surface intensities can be made:

$$I_{map,1,adjusted} = I_{map,1} + I_{map,2} + I_{adjustment} \text{ and}$$

$$I_{map,2,adjusted} = I_{map,1} + I_{map,1},$$

if $I_{map,1} > I_{map,2}$ $$I_{map,1,adjusted} = I_{map,1} + I_{map,2} \text{ and}$$

$$I_{map,2,adjusted} = I_{map,1} + I_{map,2}$$

if $I_{map,1} = I_{map,2}$ $$I_{map,1,adjusted} = I_{map,1} + I_{map,2} \text{ and}$$

$$I_{map,2,adjusted} = I_{map,1} + I_{map,2} + I_{adjustment}$$

if $I_{map,1} < I_{map,2}$.

$I_{adjustment}$ can be any positive value, for example 100.

A surface map is thus generated which not only indicates preferred points for irradiating the treatment volume in order to protect organs at risk, but also only takes into account the position of the organs at risk with respect to the treatment volume when preferably located behind and not in front of the treatment volume as viewed along the line of the radiation beam.

The transparency, lucency or opacity of a volume or voxel can be determined or can be predefined depending on one or more of the following: distance from the surface, functional aspects, the sensitivity to radiation of the structure or organ concerned; the distance from the treatment volume; and the importance of the structure or organ concerned. The transparency can for example be set to zero (or the opacity set to a maximum value) for a structure or organ which should not receive any radiation at all, such that no simulated light or ray exiting the treatment volume surface is allowed to pass through and black areas are generated on the map surface which indicate that no radiation is to be directed onto the treatment volume from this point of the map area. Conversely, tissue or organs which are less affected by radiation are modelled as exhibiting a high degree of transparency (or low opacity), thus generating a bright area on the map surface which indicates that starting irradiation of the treatment volume from this point is less harmful to the body as a whole.

The invention also relates to a program which, when running on a computer or when loaded onto a computer, causes the computer to perform the method as described above and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform all the steps of the method as described above.

The invention also relates to a planning or control system for a radiation treatment device comprising: the computer as described above, for processing the three-dimensional or volumetric image data of a body and for calculating a quantitative value for the suitability of possible radiation entry and exit points as set forth above; a data interface for receiving the three-dimensional data and optionally for outputting control data to an irradiation device; and optionally a user interface for receiving data from the computer in order to provide information to a user, wherein the received data are generated by the computer on the basis of the results of the processing performed by the computer in accordance with the method described above.

In addition, a radiation treatment device is provided which is controlled with respect to the position of the radiation-emitting element relative to the body or treatment volume, on the basis of the results of the data outputted from the computer which quantitatively indicate which relative positions or irradiation directions or points are preferred and/or less harmful as compared to other possible irradiation points or directions.

Additional advantageous features are disclosed in the following detailed description of embodiments. Different features of different embodiments can be combined.

FIG. 1 schematically shows an intensity profile being generated on a map surface in accordance with the invention;

FIG. 4 schematically shows a treatment system which can be controlled using planning data or control data generated in accordance with the invention.

Figure 1:
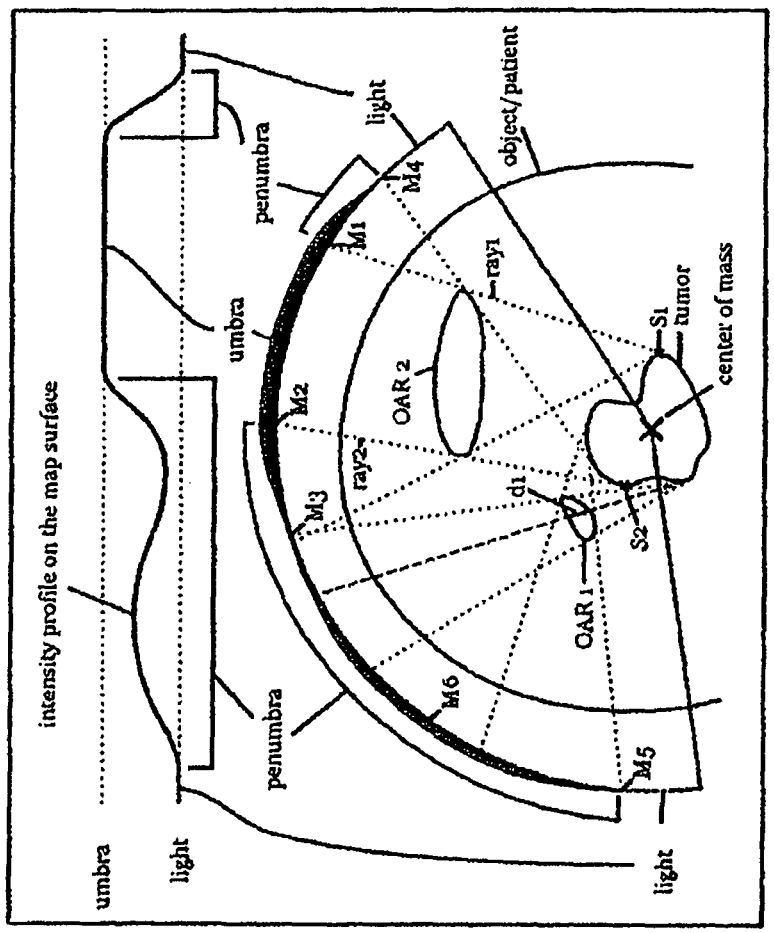

FIG. 1 shows a schematic representation of a method for generating planning or control data, wherein a cross-sectional view of an object containing a tumour as a treatment volume and containing a volume surrounding the treatment volume as a non-treatment volume including two organs at risk (OAR) is shown. It is to be noted that the boundary of the object can also be the semi-circle shown which is the map surface on which the intensity profile is depicted and will usually be between this map surface and the treatment volume, as shown in FIG. 1.

The treatment volume or tumour volume is determined, for example on the basis of a three-dimensional MRI data set which is segmented using known methods so as to also obtain the boundaries of the organs at risk shown (OAR1 and OAR2) which are located within the same body. These organs at risk OAR1 and OAR2 are to be protected from receiving a high dose of radiation or possibly even from receiving any radiation at all in the course of a radiotherapy treatment, In order to determine an expedient location on the circular map surface shown, from which an irradiation beam can be projected in a straight line towards the centre of mass of the treatment volume or tumour, the treatment volume or tumour surface is considered to emit light or rays along a straight line in all possible directions, with the exception of directions leading into the treatment volume itself. The organs at risk OAR1 and OAR2 are considered or modelled to have a predefined opacity or transparency which for example does not allow any ray emitted from the treatment volume surface to pass through or which alternatively reduces the intensity of a ray emitted from the treatment volume surface, by a specific fixed factor of for example 50%, when passing through an organ at risk, or reduces it by a factor which is determined on the basis of the distance by which a ray penetrates said organ at risk when passing through it along a straight line. The organ at risk can for example be assigned a transparency of 0.9 which would then reduce the intensity of a ray by 10% per unit length, such that for example a ray traversing this organ at risk along one unit length would be reduced in intensity by 10%, a ray traversing the organ at risk along a distance of two unit lengths would be reduced in intensity by 20%, and so on.

Depending on the vulnerability of the segmented volume or organ at risk to radiation, the transparency or opacity of the volume or picture elements or volume elements (voxels) belonging to the respective organ or non-treatment volume can be selected. If the organ is not to receive any radiation at all, the opacity is set to 100%, i.e. the transparency is set to 0%; in other words, no ray emitted from the treatment volume is allowed to pass through, thus effectively reducing the intensity of this ray to 0%.

If a structure or tissue is not appreciably affected by radiation, the transparency is set to 1 or 100%, i.e. a ray passes through it unattenuated, without its intensity being reduced.

A table showing an example set of values for non-treatment organs or tissues to be used is given below:

TABLE 1

| Structure/organ | Transparency (vulnerability) |
|---|---|
| Tissue | 100% or 1 |
| Bones | 80% or 0.8 |
| Nerve system | 5% or 0.05 |
| Blood vessel | 20% or 0.2 |
| Liver tissue | 0% or 0 |
| Pulmonary tissue | 0% or 0 |

It is to be noted that the above example is not binding or limiting and that other intensity values for a volume or voxel belonging to a particular structure can be chosen.

According to a separate, independent approach, the importance of the respective volume can be considered, wherein a voxel belonging to a particular volume is assigned an intensity which is lower, the greater the importance of the respective structure. An example of assigning transparency values is shown in Table 2 below.

TABLE 2

| Structure/organ | Transparency (importance) |
|---|---|
| Tissue | 100% or 1 |
| Bones | 90% or 0.9 |
| Nerve system | 0% or 0 |
| Blood vessel | 30% or 0.3 |
| Liver tissue | 20% or 0.2 |
| Pulmonary tissue | 10% or 0.1 |

The two approaches above, i.e. defining the transparency on the basis of the vulnerability of the volume to radiation and on the basis of the importance of the volume, can be combined if desired. Thus, if both factors are considered, the respective transparency values assigned to a respective single voxel can be multiplied, in order to obtain a combined transparency value which can be used for the subsequent calculation and simulation, according to the following formula:

$$T_{combined}(\text{voxel}) = T_{vulnerability}(\text{voxel}) * T_{importance}(\text{voxel}).$$

In accordance with another independent aspect, the transparency (or opacity) of a volumetric element can depend on the distance from the voxel to the treatment volume. It can for example be defined such that the closer the voxel is to the treatment volume, the higher the transparency of the respective voxel is set. The transparency T can for example be calculated by:

$$T = 1/d(\text{patient surface})$$

wherein d (patient surface) is the minimal distance to the surface of the patient. This distance can for example be read from a predefined distance map.

Regarding a ray exiting the treatment surface, the same approach can be used. More preferred, the length of a vector connecting the respective point with the patient surface and running through the centre of the treatment volume is chosen.

If, for example, a sphere is used as a map surface has a radius r which is the distance from the map surface to the centre of mass of the treatment volume, then the transparency of a respective voxel can be defined as:

$$T_{distance}(\text{voxel}, d) = T_0 * (r - w \cdot d)$$

where d is the distance from the voxel to the centre of mass of the treatment volume, w is a weighting factor (i.e. for example 0<w<1), and $T_0$ can be any of the aforementioned transparencies $T_{vulnerability}$, $T_{importance}$ or $T_{combined}$.

Returning to the example shown in FIG. 1, the first organ at risk OAR1 exhibits a transparency T which is calculated in accordance with one of the above formulas to be for example 50%, hence rays emitted from the treatment volume surface with an initial intensity value of $I_0$ are allowed to pass through this organ at risk OAR1 but their intensity is reduced by 50% when passing through the organ, irrespective of the distance by which the respective ray passes through the organ. In accordance with an alternative approach, the transparency is set to be 0.5 or 50% per unit length, thus causing the intensity to be reduced in accordance with the following formula:

$$I_{ray\ exiting\ OAR} = I_{ray\ entering\ OAR} * (\text{distance ray passes through OAR}) * 0.5/\text{unit length}$$

Although not shown, it is possible for a single ray to pass through more than one organ at risk, in which case the above formula is used separately and successively for each organ at risk and the respective individual transparency is used (see for example Table 1 or 2), wherein the value $I_{ray\ exiting\ OAR}$ of a more interior organ at risk is used as the value $I_{ray\ entering\ OAR}$ for the next less interior organ at risk, and so on.

An example calculation is performed, using for example hundreds of ray starting points on the treatment volume surface, wherein the rays starting from a particular starting point are directed in all possible directions or in a number of randomly selected directions. Since the treatment volume (tumour) itself is considered to be opaque, the rays do not pass through this treatment volume and are only directed towards the outside, i.e. towards the map surface.

As shown in FIG. 1, the treatment volume (tumour) has an exterior right-hand starting point S1 which is located on the treatment volume surface and an exterior left-hand starting point S2 which is likewise located on the treatment volume surface. Since the organ at risk OAR2 is considered to be an important organ and is thus assigned a transparency T of 0%, no rays starting from the treatment volume can pass through OAR2. Thus, the ray starting from the interior right-band starting point S1 and touching the exterior right-hand point of OAR2 hits the map surface at the point M1, and the ray starting at the exterior left-hand starting point S2 of the treatment volume and touching the exterior left-hand point of OAR2 hits the map surface at point M2, such that the map surface between M1 and M2 cannot be reached by any ray emitted from or starting from the treatment volume surface and following a straight line. Thus, the accumulated intensity is 0 and the intensity profile on the map surface between M1 and M2 is shown in a deep black and designated as the "umbra".

To the left of M2 in FIG. 1, the map surface can be reached by a number of rays starting from the treatment volume surface. The greater the distance from M2, the greater the amount of unattenuated rays which reach the map surface, such that the accumulated intensity of a specific point on the map surface—being the sum of the intensities of all the rays reaching this point—increases gradually with the distance of said point from M2, until a point M3 on the map surface is reached. As shown in FIG. 1, points on the map surface further to the left of M3 and as far as M5 are affected by the organ at risk OAR1, which attenuates some of the rays emitted from the treatment volume surface, such that the accumulated or summed intensity of a respective map surface point decreases towards M6, as illustrated by areas which are more thickly blackened than the area in the immediate vicinity of M3. From M6 to M5, the accumulated intensities increase again, as the attenuating effect of OAR1 decreases.

To the right of M1 in FIG. 1, an ever increasing number of rays emitted from the treatment volume surface can reach the map surface, such that the summed intensities of the respective map surface points increase to the right with the distance of the respective map surface point from M1. When the map surface point M4 is reached, which is the map surface point at which all the rays emitted from the treatment volume surface can reach the map surface unattenuated, there is no reduction in intensity and this area on the map surface can thus be designated as "light".

The same is true of the map surface area to the left of M5, where again all the rays emitted from the treatment volume surface can reach the map surface unattenuated, since neither OAR1 nor OAR2 attenuates or obstructs the emitted rays.

The areas between M1 and M4 on the right-hand side and between M2 and M5 (thus including M3 and M6) on the left-hand side can be designated as the "penumbra".

Using the intensity profile on the map surface, it is possible to determine that the best directions or angles to use for a radiation treatment of the treatment volume will be those which project radiation into the object and direct it to the centre of mass of the treatment volume or cause it to cover the entire extent of the treatment volume or tumour from the areas on the map surface identified in the intensity profile as "light", i.e. the areas to the right of M4 and to the left of M5, since no organs at risk will be affected by such radiation. The next most expedient area would be the area around M3 on the map surface which exhibits a summed intensity which is close to that of the "light" areas, although it is situated within the "penumbra" area, which means that at least one of the organs at risk OAR may be slightly affected when radiation is delivered to the treatment volume.

The "blacker" the respective area on the map surface is, the more significantly organs at risk will be affected and thus the less suitable this area is for delivering radiation. If, for example, radiation is directed to the treatment volume in the area between M1 and M2, the organ at risk OAR2 will always be directly affected, which is however to be avoided.

Figure 2:
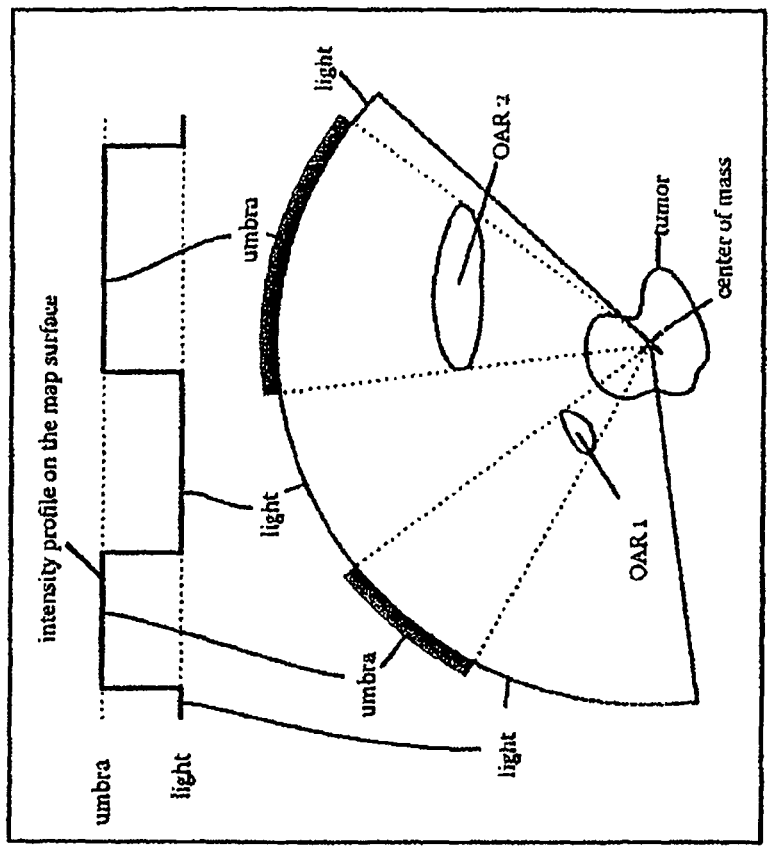
FIG. 2 shows an intensity profile being generated on a map surface in a simple manner.

FIG. 2 shows a simple example embodiment of calculating an intensity profile on a map surface, in which only the centre of mass of the treatment volume, rather than the surface of the treatment volume, is considered to be the one source of light or rays. This leads to a discrete intensity profile and possibly—as in the example shown, in which the organs at risk exhibit a transparency of 0%—to a digital intensity profile which is less suitable for identifying expedient or optimum points or directions for delivering radiation to the treatment volume.

Figure 3:
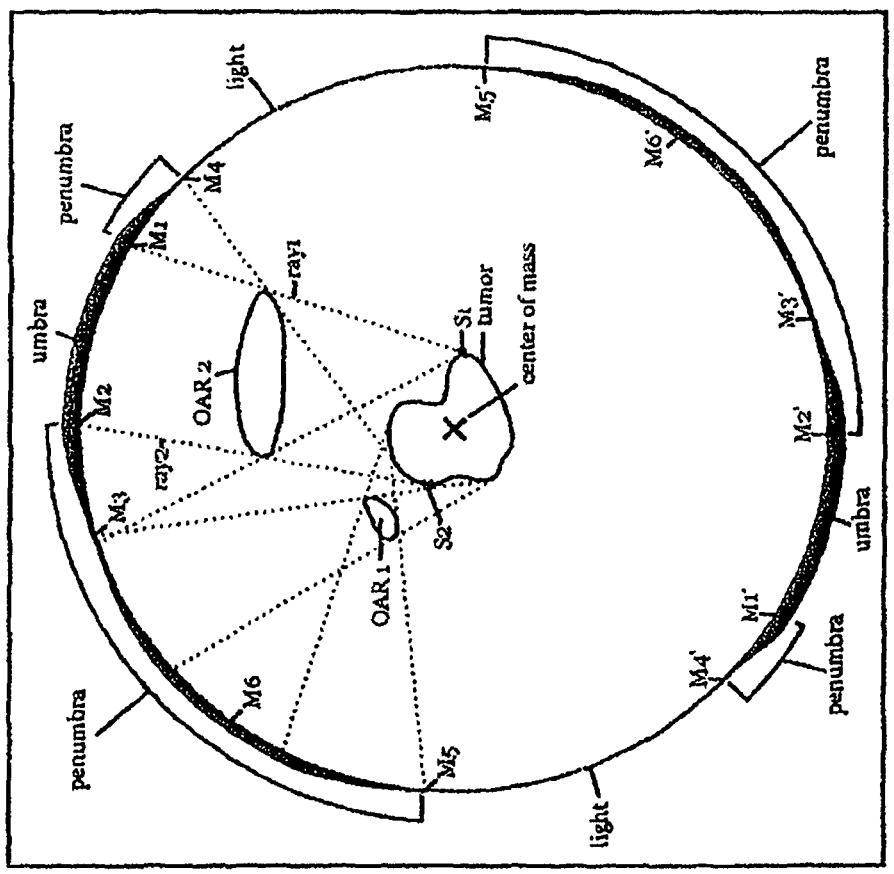
FIG. 3 shows an example embodiment based on the example of FIG. 1.

FIG. 3 shows the example from FIG. 1, but with the circle complete and representing a cross-section of the map surface. As can be seen, if OAR1 and OAR2 were the only two structures to be considered, the whole of the lower half of the map surface would exhibit the intensity profile "light", since there are no organs at risk to obstruct or attenuate the intensity of the rays emitted from the treatment volume surface to the map surface.

An irradiation beam directed onto the treatment volume from the opposite half of the map surface (the lower half in FIG. 3) and starting between points M1' and M2' (which respectively represent the points M1 and M2 as mirrored at the centre of mass) will reach the treatment volume without affecting any organ at risk. However, since the radiation will not stop at the treatment volume but rather exit the treatment volume, this irradiation beam will inadvertently affect the organ at risk OAR2, which is however to be protected from receiving any radiation.

In order to also take into account the effect of the rays exiting the treatment volume, the intensity profile on the map surface can be mirrored at the centre of mass, which is for example the point of symmetry of the map surface, or can be calculated separately. In the example shown, the penumbra and umbra intensity profile between M4 and M5 can be mirrored such that they are then also present on the opposite side between M4' and M5'. Thus, when considering the overall intensity profile on the map surface, it will be clear that the best direction or area for projecting radiation into the treatment volume is the "light" area between M4' and M5 and between M4 and M5', since the organs at risk OAR1 and OAR2 will not then be affected by any radiation at all, either before it enters the treatment volume or after it exits the treatment volume. If no such intensity profile which may be designated as "light" is available, the best area or direction for projecting radiation into the treatment volume is that which exhibits the highest summed intensity, i.e. that which is closest to the designation "light" or which is the least black, which in the example shown in FIG. 3 would be the area around M3 and the mirrored area M3' which exhibits the same (for example mirrored) or a separately calculated intensity.

It would then be preferable to use M3' as the starting point for irradiating the treatment volume rather than M3, because the slightly vulnerable organs at risk would then only receive the radiation after it had passed through and been attenuated by the treatment volume, whereas if M3 is taken as the starting point, a higher dose of radiation will reach the organ at risk first, before reaching the treatment volume. Accordingly, the intensity value at either M3 or M3' should be modified to reflect this.

Thus, in a first step when mirroring the intensity profile at the centre of mass, the accumulated or summed intensity of one point, for example M3 (receiving for example 100 rays with an average intensity value of 90, resulting in an accumulated or summed intensity of 100·90=9,000), and the summed intensity at the mirrored point, i.e. M3' (receiving for example 100 rays with an unattenuated intensity of 100, resulting in a summed intensity of 100·100=10,000), are compared.

Since it is preferable for an organ or structure which is to be protected to be located behind the treatment volume, it is advantageous to add a predefined intensity value (of for example 1,000) to the intensity value of the point or mirrored point (i.e. M3 or M3') which exhibits the highest original intensity value. In the given example, this would be the intensity value of 10,000 at point M3', which would then be corrected to 11,000.

The respective intensities of the uncorrected mirrored points are then added to the intensities of the respective points. Thus, the intensity value at the point M3 would then be 19,000 (the original intensity of 9,000 at M3 plus the original intensity of 10,000 at M3').

The intensity at M3' will thus be calculated to 20,000 (the original intensity of 10,000 at M3' plus the correction value of 1,000 plus the original intensity of 9,000 at the mirrored point M3).

Once this calculation has been performed, it is easy to determine that the overall intensity of 20,000 at M3' is higher than the overall intensity of 19,000 at M3, indicating that M3' is a more expedient starting point for irradiating the treatment volume than M3.

FIG. 4 schematically shows a radiation treatment device 1 which can be moved in a circle around the patient's body 2 which includes a treatment volume and several organs at risk, such as those exemplified in FIGS. 1 and 3. The radiation treatment device 1 emits a radiation or treatment beam 3 which is directed onto the treatment volume within the patient's body 2.

In accordance with the invention, switching the treatment beam 3 on and off and positioning the treatment device 1 at any location along the circular movement path 4 of the treatment device 1 is controlled by a controller or PC which uses the method as described above. Once the patient's body 2 has for example been registered using known methods, the treatment device 1 is moved to one or more positions between the points M4' and M5 or between the points M4 and M5' (the "light" areas from FIG. 3) and then switched on so as to emit a treatment beam 3 in order to appropriately irradiate the treatment volume, while still protecting the organs at risk.

The intensity profile on the map surface, which corresponds to the circular path 4 in FIG. 4, can also be displayed on a screen 5 which is connected to the controller or PC.

The controller or PC which is able to perform the method in accordance with the invention is also connected to a data source, such as an MRI scanner, in order to obtain raw data or pre-segmented data of the patient's body or at least of a part of the object to be treated which includes the treatment volume.

The invention claimed is:

1. A method for generating planning data or control data for a radiation treatment, the method comprising:
   a) acquiring segmented data of an object which contains a treatment volume and a non-treatment volume;
   b) modelling at least some or all of the volume or surface of the treatment volume as a source of light or rays exhibiting a predefined or constant initial intensity;
   c) modelling the non-treatment volume as comprising volumetric elements or voxels which each exhibit an individually assigned feature or attenuation value or transparency value ($t_{min} \leq t \leq t_{max}$) for the light or rays, which feature is assigned to the light or ray, which attenuation or transparency values maintain or reduce the intensity of the light or ray as it passes through the respective volumetric element or voxel, wherein the feature or attenuation value or transparency value is individually assigned to each volumetric element or voxel of the non-treatment volume;
   d) defining a map surface which surrounds the treatment volume or the object;
   e) calculating an accumulated intensity value for points or areas on the map surface, the accumulated intensity value being the sum of the intensities of all the rays which exhibit the predefined or constant initial intensity and are emitted from the volume or surface of the treatment volume and reach a respective point on the map surface by following a straight line, wherein if the ray passes through a non-treatment volume or voxel, the intensity of the respective ray is reduced or attenuated by a factor which is determined by the individual feature or attenuation value or transparency value of the respective non-treatment volume or voxel; and
   f) generating an intensity distribution on the map surface using the calculated accumulated intensity values.

2. The method according to claim 1, wherein the generating the intensity distribution on the map surface comprises generating the intensity distribution as a function of the individually assigned features.

3. The method according to claim 2, further comprising varying the individually assigned features after calculating the accumulated intensity values to calculate respective different intensity distributions on the map surface.

4. The method according to claim 1, wherein the map surface is a sphere and the centre of the sphere is located within the treatment volume or is the barycentre of the treatment volume.

5. The method according to claim 1, wherein the initial intensity of rays emerging from a part of the treatment volume or its surface is increased if the respective part of the treatment volume is determined to receive a higher dose of irradiation during later radiation treatment.

6. The method according to claim 1, wherein the treatment volume is modelled to be fully opaque, such that no ray emitted from the surface of the treatment volume passes through the treatment volume.

7. The method according to claim 1, wherein the transparency value of each non-treatment volumetric element or voxel is determined on the basis of one or more of the following:
   the vulnerability of the volume or voxel to radiation;
   the importance of the volume or voxel;
   the distance from the non-treatment volume or voxel to the treatment volume; and/or
   the distance from the non-treatment volume or voxel to the outer contour or surface of the object.

8. The method according claim 1, wherein the accumulated intensity value on a map surface point is added to the accumulated intensity value of one or each respective opposing map surface point, wherein the map surface point, the opposing map surface point and the barycentre of the treatment volume are all situated on a straight line.

9. The method according to claim 8, wherein an additional predefined intensity value is added to the accumulated intensity value of the surface point or opposing surface point which exhibits the highest original accumulated intensity value before the accumulated intensity value of the opposing map surface point is added.

10. The method according to claim 1, wherein the point on the map surface which exhibits the highest calculated accumulated intensity value ($I_{max}$) of all the points on the map surface is assigned a map surface intensity value of 100%, and map surface intensities between 0% and 100% ($I_i/I_{max}$) are calculated for the remaining points on the map surface, on the basis of this 100% map surface intensity value.

11. The method according to claim 10, wherein the areas or points on the map surface which exhibit the highest calculated accumulated intensity values are used to define one or more suitable directions for irradiating the object and/or are used to control the position and/or activation of a radiation device.

12. The method according to claim 11, wherein radiation is only directed onto the object from points or areas which exhibit a map surface intensity of 100% or more than 95%, 90%, 85% or 80%.

13. The method according to claim 12, wherein volumetric, raycasting is used to generate a continuous intensity distribution on the map surface.

14. A non-transitory computer-readable program storage medium on which a program is stored which, when running on a computer or when loaded onto the computer, causes the computer to perform a method for generating planning data or control data for a radiation treatment, the method comprising:
  a) acquiring segmented data of an object which contains a treatment volume and a non-treatment volume;
  b) modelling at least some or all of the volume or surface of the treatment volume as a source of light or rays exhibiting a predefined or constant initial intensity;
  c) modelling the non-treatment volume as comprising volumetric elements or voxels which each exhibit an individually assigned feature or attenuation value or transparancy value ($t_{min} \leq t \leq t_{max}$) for the light or rays, which feature is assigned to the light or ray, which attenuation or transparency values maintain or reduce the intensity of the light or ray as it passes through the respective volumetric element or voxel, wherein the feature or attenuation value or transparency value is individually assigned to each volumetric element or voxel of the non-treatment volume;
  d) defining a map surface which surrounds the treatment volume or the object;
  e) calculating an accumulated intensity value for points or areas on the map surface, the accumulated intensity value being the sum of the intensities of all the rays which exhibit the predefined or constant initial intensity and are emitted from the volume or surface of the treatment volume and reach a respective point on the map surface by following a straight line, wherein if the ray passes through a non-treatment volume or voxel, the intensity of the respective ray is reduced or attenuated by a factor which is determined by the individual feature or attenuation value or transparency value of the respective non-treatment volume or voxel; and
  f) generating an intensity distribution on the map surface using the calculated accumulated intensity values.

15. A computer comprising the program storage medium of claim 14.

16. A planning or control system for a radiation treatment device comprising:
  the computer according to claim 15 for processing the three-dimensional or volumetric image data of a body and for calculating a quantitative value indicating the suitability of possible radiation entry and exit points; and
  a data interface for receiving the three-dimensional data.

17. The planning or control system of claim 16, further comprising the data interface outputting control data to an irradiation device.

18. The planning or control system of claim 16, further comprising:
  a user interface configured to receive data from the computer to provide information to an associated user, wherein the received data are generated by the computer on the basis of the results of the processing performed by the computer in accordance with the program stored on the program storage medium.

19. A radiation treatment device comprising the computer of claim 15, wherein the radiation treatment device is controlled with respect to the position of the radiation-emitting element relative to the body or treatment volume and/or with respect to the activation of the radiation-emitting element on the basis of the results of the data outputted from the computer which quantitatively indicate which relative positions or irradiation directions or points are preferred and/or less harmful as compared to other possible irradiation points or directions.

* * * * *